United States Patent
Hasselberg et al.

(10) Patent No.: US 11,521,735 B2
(45) Date of Patent: Dec. 6, 2022

(54) DELIVERING INDIVIDUALIZED MENTAL HEALTH THERAPIES VIA NETWORKED COMPUTING DEVICES

(71) Applicant: University of Rochester, Rochester, NY (US)

(72) Inventors: Michael J. Hasselberg, Rochester, NY (US); Wendy Cross, Rochester, NY (US); Matthew Brown, Rochester, NY (US); David John Mitten, Rochester, NY (US); Christopher John Dasilva, Rochester, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 273 days.

(21) Appl. No.: 16/909,358

(22) Filed: Jun. 23, 2020

(65) Prior Publication Data
US 2020/0402642 A1   Dec. 24, 2020

Related U.S. Application Data

(60) Provisional application No. 62/865,252, filed on Jun. 23, 2019.

(51) Int. Cl.
*G16H 20/70* (2018.01)
*G16H 40/67* (2018.01)
(Continued)

(52) U.S. Cl.
CPC ............ *G16H 20/70* (2018.01); *G16H 10/60* (2018.01); *G16H 40/67* (2018.01); *G16H 80/00* (2018.01)

(58) Field of Classification Search
CPC ........ G16H 20/70; G16H 10/60; G16H 40/67; G16H 80/00
See application file for complete search history.

(56) References Cited

U.S. PATENT DOCUMENTS

2017/0004260 A1*   1/2017   Moturu ................. G16H 10/60
2018/0121728 A1*   5/2018   Wells ................. G02B 27/0176
(Continued)

FOREIGN PATENT DOCUMENTS

WO   WO-2020236407 A1 *   11/2020   ............. G16H 10/20

OTHER PUBLICATIONS

Freeman et al., Virtual reality in the assessment, understanding, and treatment of mental health disorders, 2017, Cambridge University Press, Psychological Medicine 47(14), pp. 2393-2400. (Year: 2017).*

(Continued)

*Primary Examiner* — Jeffery A Brier
(74) *Attorney, Agent, or Firm* — Kilpatrick Townsend & Stockton LLP

(57) ABSTRACT

Aspects and features of this disclosure relate to delivering individualized mental health therapies via networked computing devices. A mental-health-treatment-delivery server outputs a module with video content in connection with a mental health treatment protocol for a user. The mental-health-treatment-delivery server outputs a request for the user to respond to a question or to stimuli. The mental-health-treatment-delivery server receives a response from the user to the question or the stimuli. The mental-health-treatment-delivery server compares the response to stored data to determine information to present to the user. The mental-health-treatment-delivery server receives a command from the server device to present the information to the user. The mental-health-treatment-delivery server outputs the information to an interface of the user device.

20 Claims, 8 Drawing Sheets

(51) Int. Cl.
  *G16H 80/00* (2018.01)
  *G16H 10/60* (2018.01)

(56) References Cited

U.S. PATENT DOCUMENTS

| | | | |
|---|---|---|---|
| 2018/0132776 A1* | 5/2018 | Flickinger | A63F 13/46 |
| 2019/0206518 A1* | 7/2019 | Banerjee | G16H 40/67 |
| 2020/0302825 A1* | 9/2020 | Sachs | G09B 5/02 |

OTHER PUBLICATIONS

Cikajlo et al., A Cloud-Based Virtual Reality App for a Novel Telemindfulness Service: Rationale, Design and Feasibility Evaluation, 2017, JMIR research protocols vol. 6 issue 6 e108, pp. 1-16. (Year: 2017).*

Alina Huldtgren, Christina Katsimerou, Andre Kuijsters, Judith A. Redi, and Ingrid E.J. Heynderickx, Design Considerations for Adaptive Lighting to Improve Seniors' Mood, Jun. 10, 2015, In 13th International Conference on Smart Homes and Health Telematics, ICOST 2015, Proceedings, Springer, pp. 15-26. (Year: 2015).*

Cella et al., Initial Adult Health Item Banks and First Wave Testing of the Patient-Reported Outcomes Measurement Information System (PROMIS™) Network: 2005-2008, Journal of Clinical Epidemiology, vol. 63, No. 11, Nov. 2010, pp. 1179-1194.

Cohen, The Concentration of Health Care Expenditures and Related Expenses for Costly Medical Conditions, Agency for Healthcare Research and Quality, Available Online at—https://meps.ahrq.gov/data_files/publications/st455/stat455.pdf, Oct. 2014, 8 pages.

Henderson, Developing an Integrated Computerized CBT Virtual Reality Platform for Treatment of Behavioral Health Conditions, University of Rochester Presentation, Apr. 2018, 1 page.

Ojeda et al., Gender, Race-Ethnicity, and Psychosocial Barriers to Mental Health Care: An Examination of Perceptions and Attitudes among Adults Reporting Unmet Need, Journal of Health and Social Behavior, vol. 49, No. 3, Available Online at—https://www.jstor.org/stable/27638759, Sep. 2008, pp. 317-334.

Weiler, Ama Adopts Principles to Promote Safe, Effective mHealth Applications, American Medical Association, Available Online at—https://www.ama-assn.org/ama-adopts-principles-promote-safe-effective-mhealth- applications, Nov. 16, 2016, 5 pages.

Wierson, No More Time on the Couch: The Rise of Digital Mental Health Therapeutics, Observer, Available Online at—https://www.dhitglobal.org/no-more-time-on-the-couch-the-rise-of-digital-mental-health-therapeutics/, Apr. 22, 2019, 23 pages.

* cited by examiner

DELIVERING INDIVIDUALIZED MENTAL HEALTH THERAPIES VIA NETWORKED COMPUTING DEVICES

CROSS-REFERENCE TO RELATED APPLICATION

This claims the benefit to U.S. Provisional Application No. 62/865,252 filed on Jun. 23, 2019, titled "Delivering Individualized Mental Health Therapies Via Networked Computing Devices," the disclosure of which is hereby incorporated by reference in its entirety for all purposes.

TECHNICAL FIELD

The present disclosure relates generally to systems and methods for delivering individualized mental health therapies. More specifically, but not by way of limitation, this disclosure relates to individualizing a mental health therapy by leveraging database relationships.

BACKGROUND

The demand for psychological treatment for biobehavioral responses to anxiety and stress has expanded significantly as high-stress work environments, financial instability, and other factors have caused mental health challenges for a widespread population. However, a lack of trained therapists, stigma, cost, and geographic barriers can result in many patients remaining untreated. Using certain examples of the present disclosure can ameliorate these barriers by leveraging technology to extend behavioral health service delivery outside of traditional clinic walls.

SUMMARY

In one example, a method of delivering an individualized mental health treatment using networked devices is disclosed. The method includes receiving, at a server device, at least one response to a question or stimuli presented to a user in connection with a mental health treatment application executing on a user device. The method also includes comparing the at least one response to stored user data to determine information to be presented to the user. The method also includes outputting an instruction for causing the mental health treatment application to output the information to the user. The method also includes transmitting data about use of the mental health treatment application by the user to an electronic health record system.

In another example, a system includes a processor and a non-transitory memory device communicatively coupled to the processor. The processor receives instructions that cause the processor to perform operations for delivering an individualized mental health treatment using networked devices. The system includes a user device that outputs a module with video content in connection with a mental health treatment protocol for a user. The system outputs a request for the user to respond to a question or to stimuli. The system receives a response from the user to the question or the stimuli. The user device transmits the response to a server device for comparing the response to stored data to determine information to present to the user. The user device receives a command from the server device to present the information to the user. The system outputs the information to an interface of the user device.

In a further example, a non-transitory computer-readable medium includes a processor device. The non-transitory computer-readable medium includes a mental health treatment application that outputs, by an interface of a user device, a module with video content in connection with a mental health treatment protocol for a user. The mental health treatment application outputs a request for the user to respond to a question or to stimuli. The mental health treatment application receives a response from the user to the question or the stimuli. The mental health treatment application transmits the response to a server device for comparing the response to stored data to determine information to present to the user. The mental health application receives a command from the server device to present the information to the user. The mental health application outputs the information to an interface of the user device.

DETAILED DESCRIPTION

Figure 1:
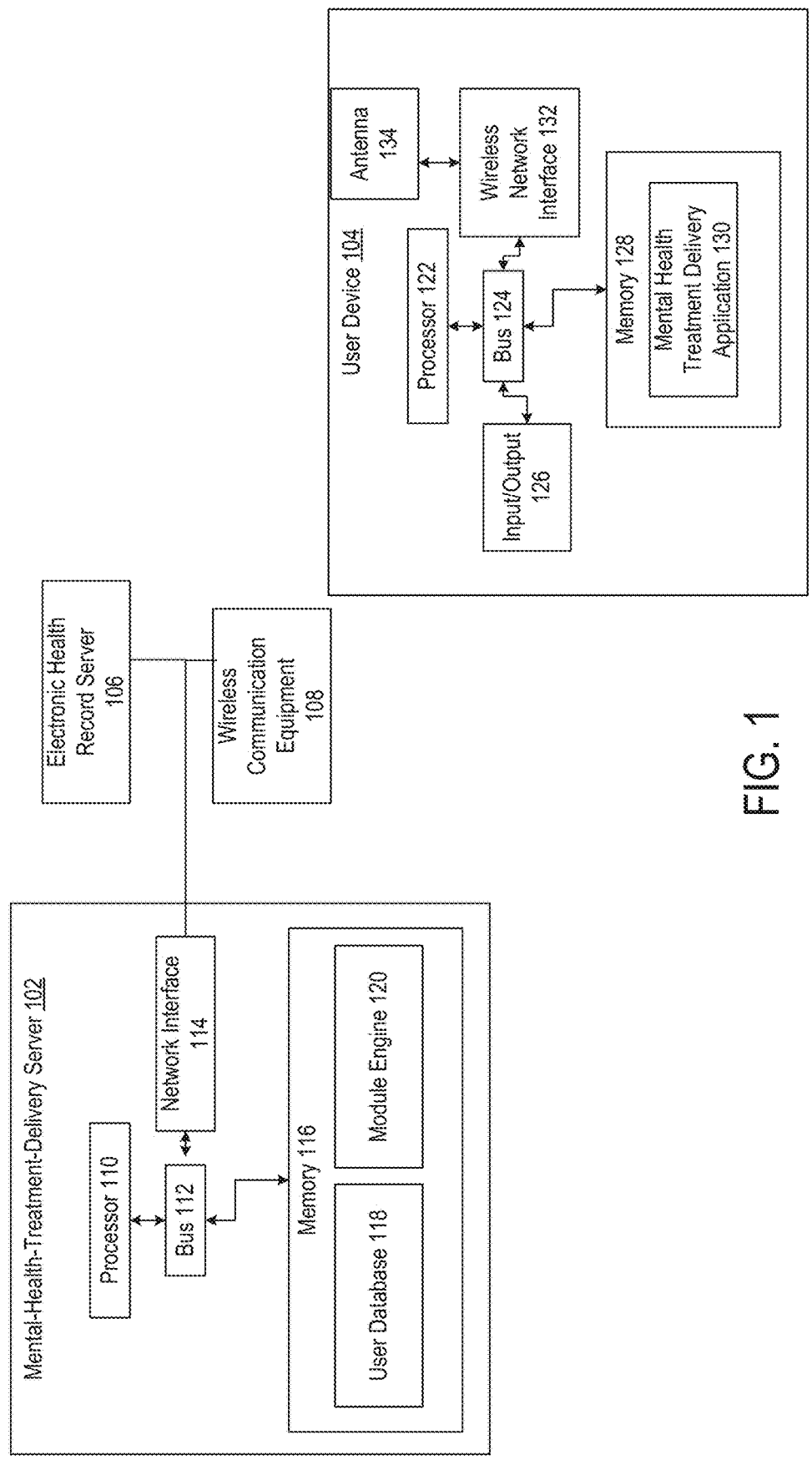
FIG. 1 is a diagram of a computing environment for an individualized medical health treatment system according to some aspects of the present disclosure.

Certain aspects and features relate to delivering individualized mental health therapies by leveraging patient-reported outcome data collection, electronic health record (EHR) integration, and patient responses to visual or auditory stimuli. An example of a mental health therapy is cognitive behavioral therapy (CBT) by which a virtual therapist can deliver treatment modules to a patient and answers from the patient to questions and perception of stimuli can be used by the system to modify information that is delivered to the patient.

In one example, a system can be implemented via a mobile device application platform to provide an evidence-based behavioral health therapy that can displace the requirement of fully engaged live clinicians or costly medications. A system, according to some examples, can be focused on the management of anxiety and stress. Behavioral health conditions in some areas are the third most frequently diagnosed condition in emergency departments, and those admitted into the hospital are 22% more likely to be readmitted than those without comorbid mental illness. Despite the growing evidence that psychiatric care is valuable, few adults with behavioral health conditions get treatment due to lack of access. By using one or more examples of the present disclosure, access to behavioral health care can be increased.

CBT is a psychological treatment for biobehavioral responses to anxiety and stress. CBT can be a time-limited psychotherapeutic approach that focuses on the relationships among cognitions, emotions, and behaviors, and encourages patients to adopt an active problem-solving approach to cope with distress. This treatment approach can improve functioning and quality of life for patients with anxiety symptomology. To be effective and to encourage patient adherence to the treatment protocol, a system, according to some examples, can be integrated with the patient's EHR to provide data security, can include virtual reality features and pleasing, individualized stimuli, and can use patient feedback and answers to questions to determine information to provide to the patient. Given the limited availability of providers and therapists, innovative behavioral health interventions, such as a system according to some examples of the present disclosure, can be used to meet growing service demands. Patient access can be increased, costs can be decreased, and the shortage of providers can be alleviated. Integration with an EHR system can allow the quantifiable clinical impact of various examples of the system to measured, as well as its impact on patient engagement. Analyzing associations among behavioral and physical health symptoms, interventions, and outcomes can be possible and can provide the basis for developing data-driven risk stratification of patient populations with behavioral health needs. Embedding a system according to various examples with the EHR system can allow for automated provider documentation and guide care pathways used to intervene with appropriate level clinical solutions earlier and more effectively.

In one example, a system includes a software application that can execute on a user device, such as a mobile phone with computing functionality, and includes a server subsystem that can dynamically control the application and provide content for delivery by the application to the user. The server subsystem can also link to an EHR subsystem to leverage the data security, data relationships, and provider information in the EHR subsystem. An application, according to some examples, can include eight modules arranged in a sequence of weekly lessons that progressively build upon the previous lesson to encourage mastery of dysfunctional thoughts, emotions, and behaviors associated with stress and anxiety. Each module can include a series of virtual reality psychotherapy, animated videos, and images that illustrate the principles of CBT, supplementary material, and skills practice homework assignments. Before and after completion of each module, the user can complete a patient-reported outcome assessment. Results from this assessment can be used to maximize the precision of the modules for the particular user based on what is known about the user from previous questions to tailor the intervention to meet the user's individual needs. The data from the system can be used to produce a roadmap identifying the type of patients that may need a higher (or lower) level of care and to identify patients that may be at increased risk for poor outcomes. This can result in effective coordination and triage of patients to the appropriate level of care based on patient reported needs. Users may also receive automated reminders via the EHR to engage in the application, and clinical progress reports can be available for download after the completion of each module.

Detailed descriptions of certain examples are discussed below with reference to the figures in which like numerals indicate like elements to describe the illustrative examples but, like the illustrative examples, should not be used to limit the present disclosure.

FIG. 1 is a diagram of a computing environment for an individualized medical health treatment system according to some aspects of the present disclosure. The computing environment includes a mental health treatment delivery server 102, a user device, an electronic health record server 106, and various wireless communication equipment 108. The mental health treatment delivery server 102 may provide therapy modules to the user device. The mental health treatment delivery server 102 may connect with an electronic health record server 106 to access an electronic health record of a patient associated with the user device. The user device may receive therapy modules from the mental health treatment delivery server 102 and present them to a user.

The mental-health-treatment delivery server 102 may contain various elements including a processor 110 and memory 116. The processor may be coupled to the memory storage via a communication bus 112. The processor may also be coupled to a wireless network interface 114 for communicatively coupling to other components of the computing environment, for example, the user device. The mental-health-treatment-delivery-server may include a user database 118 (e.g., patient database) and a module engine 120. In one example, the user database 118 may store detailed profile information regarding various medical therapy providers (e.g., name, license, practice information) or patients (e.g., name, medical status, current provider, prescribed therapy, patient risk classification, etc.). The module engine 120 may provide the client device with a module that includes parameters for a virtual therapist office, a customizable environment (e.g., location, ambient sounds, etc.) or other environment that the user may perform various interactions within as described in some aspects of the disclosure.

The user device may be any suitable computing device for receiving a therapy module and presenting the therapy module to a user. For example, a user device may download or stream a therapy module from the mental-health-treatment-delivery-server. In one example, the user device stores the therapy module in a mental health treatment application 130. The user device may present the therapy module in the mental health treatment application 130 to a user using audio, video, or location cues. For example, the user device may present a video of a therapy module. In some examples, the video may be a 360 degree video or virtual reality (VR) environment. The user device may record interactions with the user and the therapy module to store in mental health treatment application 130.

In some cases, the user device may interact with the mental-health-treatment-delivery-server via an application programming interface, a cloud-based application, or a standalone application that is downloaded to the user device from the mental-health-treatment-delivery-server. The user device may access the mental-health-treatment-delivery-server via various networking interfaces, direct communication protocols, or existing medical protocols. The user device may include a processor 122 communicatively coupled by a communication bus 124 to a memory storage 128, various input/output connectors 126, a wireless network interface 132, and an antenna 134.

In one example, the electronic health record server 106 stores multiple electronic health records for various patients. For instance, the electronic health record server 106 may store a group of patients being treated for a set of health conditions, a group of patients being treated within a specific geographic region, or a group of patients being treated by a set of defined providers (e.g., a health system, a private practice, a group of private practices, etc.).

The mental health treatment delivery server 102 and the user device may communicate via a communication network, which in some configurations is a wireless internet connection. In some examples, the user device may also connect to the electronic health record server 106 via an internet portal or application programming interface. In some cases, the mental-health-treatment-delivery-server may perform authentication of the client device or user by prompting for a credential to submit to the electronic health record server 106. In other cases, the mental-health-treatment-delivery-server may send a client device ID (e.g., IMEI, IP address, MAC address, etc.) to the electronic health record server 106 (e.g., electronic health record system).

In one example, the mental-health-treatment-delivery server 102 may determine relationships between data structures on the electronic health record server 106, the user database 118, and data collected on the user device 104 relating to delivery of a treatment module. For instance, the electronic health record server 106 may store user data, such as medical or demographic information associated with a plurality of patients in a data structure grouped by health record. The user database 118 may be a database that includes information that identifies a particular user, a role of the user such as patient, therapist, support staff, etc., medical classification, and other information about the user. The mental-health-treatment-delivery server 102 can extract features from the data collected on the user device 104 to determine values for incorporation in the medical record. The mental-health-treatment-delivery server 102 can further determine that particular values are anomalous or outside of a normalized range for a user. The mental-health-treatment-delivery server 102 can flag that patient record on electronic health record server 106 for review by a therapist for values that indicate a change in medical condition of the user. In some examples, the mental-health-treatment-delivery server 102 can flag that patient record on the electronic health record server 106 for review by an administrator of the electronic health record server 106 for values that indicate a corrupted file, data breach, or other errors that do not indicate a medical change in the user.

In some cases, mental-health-treatment-delivery server 102 can determine that features of a stress level, such as stress factors that are used to compute a stress level, may be integrated into electronic health record server 106. The mental-health-treatment-delivery server 102 can analyze records of electronic health record server 106 to determine a change in user performance over a time period associated with delivering mental health treatment to a particular user.

In other cases, the electronic health record server 106 may be integrated into the mental-health-treatment-delivery server 102. For example, the mental-health-treatment-delivery server 102 may store a portion, up to and including, an entire record associated with a user device 104 ID that is delivering the individualized mental health treatment. The mental-health-treatment-delivery server 102 can also compute features or statistics from health records of a user to assess efficacy of treatment modules across a population of similar users receiving similar treatment modules.

Figure 2:
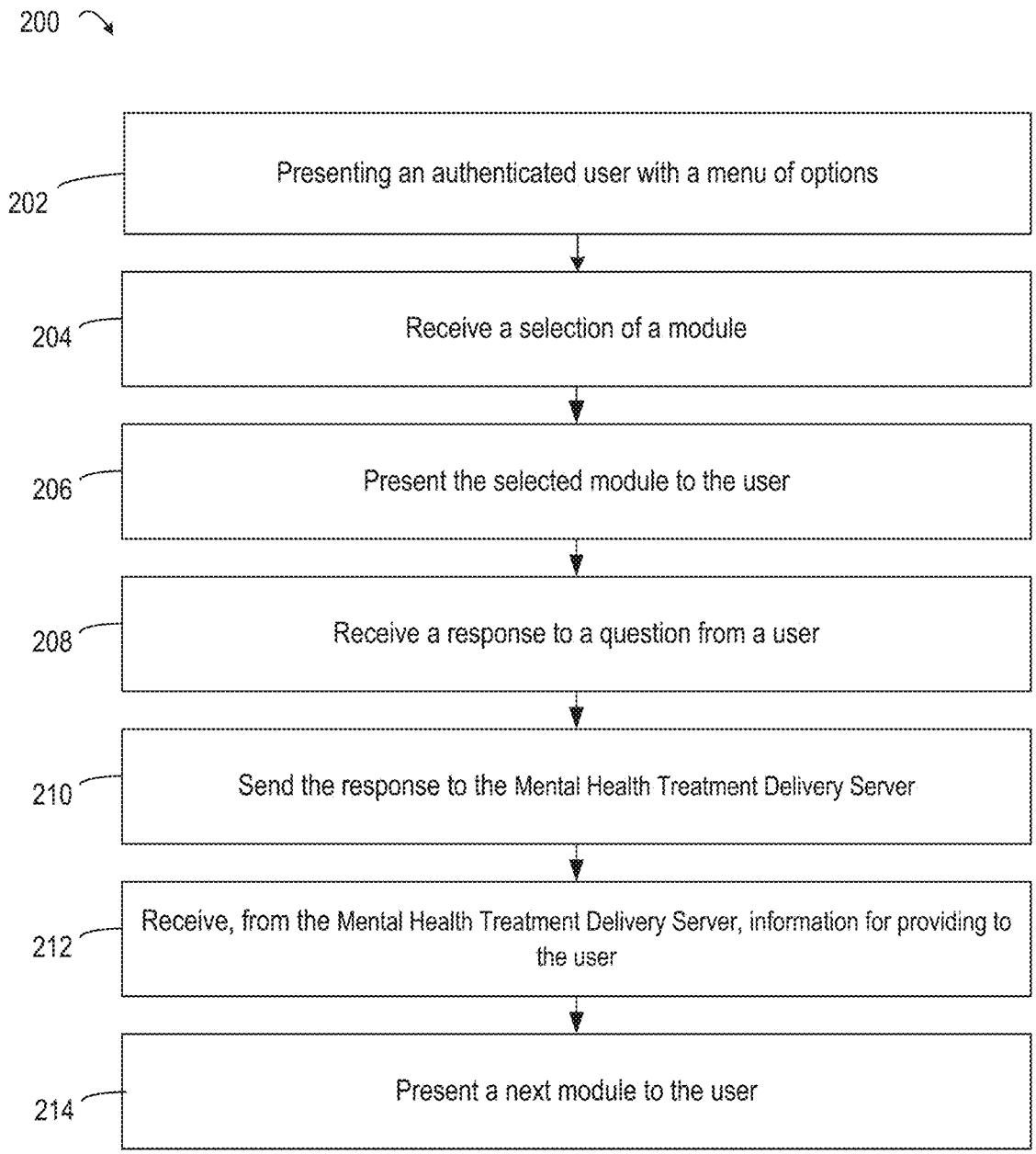
FIG. 2 depicts a flowchart of a process for presenting modules to a user, according to some aspects of the disclosure.

FIG. 2 depicts a flowchart of a process 200 for presenting modules to a user, according to some aspects of the disclosure. For example, the user device may include a processor that executes operations to accomplish one or more blocks of the process 200.

At block 202, the process 200 involves presenting an authenticated user with a menu of options. In one example, a user device may request authentication credentials (e.g., a username and password combination, a patient ID, a certificate, etc.) from a user. The user device may verify the authentication credentials and present a menu of options to the user. The menu of options may contain options that correspond to a module of mental therapy treatment. In some cases, the user device may adjust the menu of options based on a particular user that has been authenticated or a previous session of use. For instance, the user device may modify the presented menu of options based on previously completed modules, additional modules unlocked by past session completion (e.g., a usage streak, a completion percentage, etc.), or other factors relating to the authenticated user. In one aspect, a user device may have multiple user profiles associated with corresponding mental therapy treatments. In a configuration with multiple users associated with a user device, the user device may use authentication credentials unique to each user of the user device.

In another example, the user device may have identifying information of the user (i.e., the patient) stored in a memory storage component of the user device. The user device may send a portion of the identifying information (e.g., patient profile number, provider assignment information, etc.) to the mental-health-treatment-delivery-server for authentication purposes. The mental-health-treatment-delivery-server may identify a particular patient record from multiple patient records. The mental-health-treatment-delivery-server may associate the user device with the particular patient record and allow the user device to access stored data relating to the particular patient record.

At block 204, the process 200 involves receiving a selection of a module. For instance, the user device may receive a selection of a module from a user. An example of receiving the selection may be an input selection (e.g., a touchscreen gesture, a gaze target gesture, a button/mouse click, etc.).

At block 206, the process 200 involves presenting the selected module to the user. For example, the selected module may be content of a therapist giving a mental therapy session. In one aspect, the selected module may include a mental health therapy treatment. Examples of modules include a therapist discussion of a particular therapy topic, natural scenes, or situational scenes to elicit a cognitive response from a user. In one example, the selected module may be a segment of video content of a therapist with a corresponding segment of audio content. In one configuration, the segment of video and audio content may be 360 degree video and associated 360 degree video presented in a virtual reality setting.

In one example, the therapy module may be a video presentation of an office environment with a cognitive therapy provider. The therapy module may include various objects commonly found in a medical therapy environment. In some cases, the office environment may have chairs, desks, a reception area, and a provider character. In this example, the video presentation may be a VR environment of an office of the cognitive therapy provider. In other examples, the video presentation may be synthetically generated from a set of parameters such as a script, a provider office layout, or other environmental variables.

At block 208, the process 200 involves receiving a response to a question from a user. For example, the user device may provide one or more questions to record a user mental response to a module that was presented, for example, the module presented by block 206. The user device may present any number of questions to the user. In some examples, the questions may relate to a current stress level of the user, a characterization of the stress or mental emotions experienced within a particular timeframe (e.g., last week, last month, last year, etc.). The user device may receive the responses to the question by detecting a user interaction (e.g., a touchscreen gesture, a gaze target gesture, a button/mouse click, etc.). The user device may store the response in a memory of the user device.

The user device may record the responses as well as other characteristics related to the responses (e.g., time to respond, positioning of selection tool over other choices prior to response, click speed, etc.). The user device may send the recorded responses to the electronic health record server 106 for incorporation of the received data into the health record of the patient.

At block 210, the process 200 involves sending the response to the mental-health-treatment-delivery-server. For example, the user device may send the user response to the question presented at block 208 to the mental-health-treatment-delivery-server. In one aspect, the user device may send each response of a user to a question, while in other aspects, the user device may aggregate responses and send a group of responses. The user device may send the response to the mental-health-treatment-delivery-server via a wireless network, internet protocol, or other electronic communication method.

At block 212, the process 200 involves receiving, from the mental-health-treatment-delivery-server, information for providing to the user. For example, the user device may receive information from the mental-health-treatment-delivery-server and present the information to the user. An example of the information may be feedback on a user's progress throughout the modules (e.g., a user's stress metric compared to other users/medical averages, a user's improvement/degradation over a time period, etc.). The user device may present the information by generating a chart or video summary of the information. In one configuration, the user device may generate a chart of the information received over a time period (e.g., a user's performance over the last month). The information received by the user device may be specific feedback for each user tailored to the particular user's responses.

At block 214, the process 200 involves presenting a next module to the user. For example, the next module may be a subsequent segment of content in a prescribed therapy treatment. For example, the next module may be a predetermined segment of content that is designated to be presented after the selected module of content (e.g., the module selected in block 204). The user device may present the next module in a similar manner as described with regard to block 206.

Still referring to block 214, alternatively, the mental-health-treatment-delivery-server may determine a next module of content based at least in part on the responses received from the user. For example, the user device may send responses to the mental-health-treatment-delivery-server that indicate a particular user is experiencing an abnormally high level of stress/anxiety compared to previous responses from the particular user. The mental-health-treatment-delivery-server may determine that a particular module from the module engine 120 may be more effective in treating the user and designate the particular module as the next module. In some cases, the mental-health-treatment-delivery-server may modify a predefined sequence of modules to accommodate the particular module for the particular user.

Figure 3:
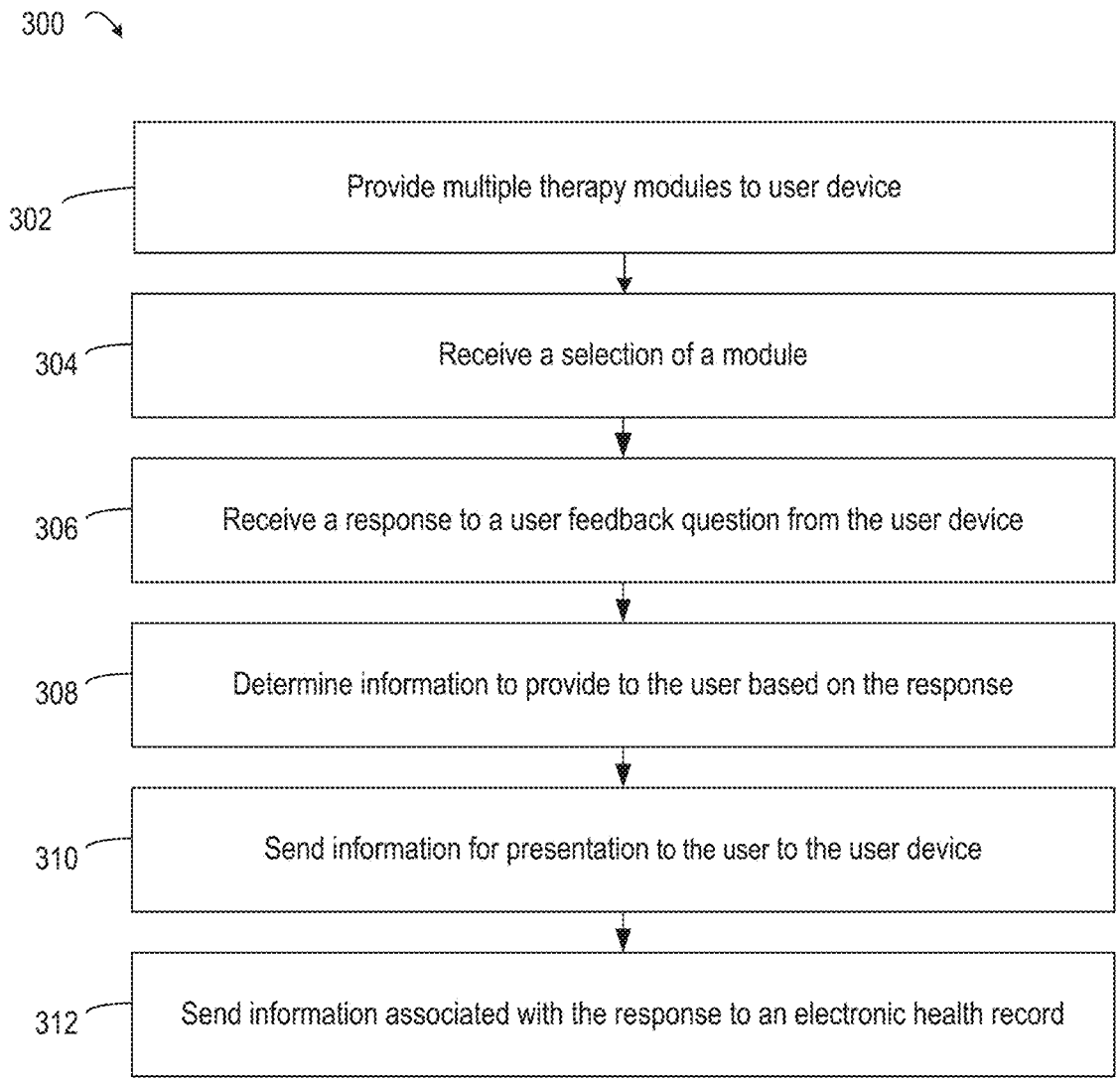
FIG. 3 depicts a flowchart of a process for providing a medical therapy to a user device according to some aspects of the disclosure.

FIG. 3 depicts a flowchart of a process 300 for providing a medical therapy to a user device according to some aspects of the disclosure.

At block 302, the mental-health-treatment-delivery-server provides multiple therapy modules to a user device. For instance, the mental-health-treatment-delivery-server may register a user device to receive a prescribed medical therapy. In one example, the user device may register with the mental-health-treatment-delivery-server by sending a captured quick response (QR) code from a camera of a user device. In some examples, the QR code corresponds to a particular set of modules in a medical therapy. The mental-health-treatment-delivery-server may associate the user device with the QR code such that an electronic health record of a user associated with the user device may be accessed. The mental-health-treatment-delivery-server may provide multiple therapy modules to the user device by providing a digital content asset that can be downloaded or streamed. In some cases, the mental-health-treatment-delivery-server may provide the entire particular set, or any portion thereof, to the user device. The mental-health-treatment-delivery-server may alternatively provide an application to the user device that provides access to multiple therapy modules.

Alternatively, the mental-health-treatment-delivery-server may provide a library of therapy modules for download by the user device allowing the user device to provide a mental therapy in the absence of a network connection.

At block 304, the process 300 involves receiving a selection of a module. In one example, the mental-health-treatment-delivery-server may receive a selection of a module from the user device and provide the module to the user device. The mental-health-treatment-delivery-server may store the selected module in a memory storage, in some examples, in the module engine 120. In a particular configuration, the mental-health-treatment-delivery-server may provide multiple therapy modules to the user device at block 302, and provide access information (e.g., an unlock key, a progress indication, etc.) that enables the user device to access the selected module.

In another example, the selection of a module may be automated by classifying a patient into a clinical category in a mental health treatment application 130 on the user device. For instance, the user device may present the mental health treatment application 130 to the user (i.e., the patient) and provide an initial screening questionnaire or evaluation to determine an appropriate initial classification of the patient. One example of the classification may be determining whether the patient is "high stress", "moderate stress", or "low stress" through a series of cognitive evaluation questions. In an alternative configuration, a provider (i.e., a licensed therapist) can provide an initial classification of the patient to the mental health treatment application 130 by entering an initial classification into the electronic health record server 106. The user device may access the initial classification as part of the electronic health record on the electronic health record server 106.

At block 306, the process 300 involves receiving response to user feedback questions from the user device. For example, the mental-health-treatment-delivery-server may receive a response to a user feedback question from the user device via a network or wireless communication protocol. The mental-health-treatment-delivery-server may receive a set of responses in a group from the user device. The mental-health-treatment-delivery-server may store the response in a memory storage. In some cases, the mental-health-treatment-delivery-server may record the response from the user device in the electronic health record server 106 as described with regard to block 312.

At block 308, the process 300 involves determining information to provide to the user based on the response. For example, the mental-health-treatment-delivery-server may analyze the response received from the user device to determine various information to provide to the user. For instance, the mental-health-treatment-delivery-server may determine that a stress level of a user has increased or decreased with regard to a previous response of the user, an average of stress levels, or both. The mental-health-treatment-delivery-server may determine to provide information relating to a visual indication of the change in stress level of the user to the user device. The mental-health-treatment-delivery-server may provide to the user device a historical plot of stress levels for the user or an indication of the change of a previous stress level to the current stress level of the user. In some configurations, the mental-health-treatment-delivery-server may determine that the response of a particular user necessitates medical escalation such as emergency treatment. The mental-health-treatment-delivery-server may provide information relating to an escalation (e.g., therapist call number, emergency department contact information, additional resources) of medical care. In other configurations, the mental-health-treatment-delivery-server may provide an additional segment of content to the user based on the responses. In some cases, the mental-health-treatment-delivery-server may determine that an increase or decrease of a stress level of the user has occurred and provide a segment of content to the user device that specifically reflects that level of self-reported distress along with tailored encouragement.

In one example, the mental health treatment deliver server may provide the user device information regarding presentation of subsequent modules based on the user's response. For instance, the mental-health-treatment-delivery-server may provide information that modifies the various aspects of the presented module including environmental visual cues, the environmental audio cues, or both. For instance, the mental-health-treatment-delivery-server may provide information to the user device that indicates the user device should modify the visual lighting intensities to simulate conducting medical therapy sessions at various times of day, various weather conditions, or office environment lighting conditions. In some cases, the mental-health-treatment-delivery-server may additionally or alternatively modify the audio cues.

Still referring to block 306, the mental-health-treatment-delivery-server may provide information to the user device to indicate the user device should display a non-verbal cue to notify the user that an interaction with a supplemental module is available. In some cases, interactions with a supplemental module may involve performing a medical therapy exercise such as word association, patient reported feedback, or other clinical activities.

At block 310, the process 300 involves sending information for presentation to the user to the user device. For example, the mental-health-treatment-delivery-server may provide the information to the user device relating to the response of the user to the feedback question. In some cases, the mental-health-treatment-delivery-server may provide multiple types of information to the user device. Examples of information that may be provided to the user device are described with reference to block 308.

In some cases, the mental-health-treatment-delivery-server may also notify the licensed therapist (e.g., according to a patient profile) that an anomalous response has been received from the patient. In other cases, the mental-health-treatment-delivery-server may provide additional features such as other modules with customizable content (e.g., visual or audio cues) based on preferences of the patient. For instance, a patient that has provided responses indicating to the mental-health-treatment-delivery-server that the patient is moving to an elevated stress level, such as a higher than an average stress level of the user, the mental-health-treatment-delivery-server may prompt that patient to view a calming module of content presented by the client device.

The mental-health-treatment-delivery-server may provide individualized feedback unique to the particular patient that indicates improved or degraded performance of the patient. The mental-health-treatment-delivery-server may also provide an additional content item based on the magnitude of the improvement or degradation (i.e., an encouragement content item to reinforce the behavior(s) or an admonishment content item to reduce the behavior(s)). In some cases, the patient may present a significant degradation in performance or increase in stress. In such a case, the mental-health-treatment-delivery-server may provide an emergency notification to the client device to provide emergency or urgent escalation of treatment to the patient. An example of an emergency notification is a phone number or immediate contact information for a licensed therapist to escalate the treatment.

At block 312, the process 300 involves sending information associated with the response to an electronic health record stored in an electronic health record server 106. For example, the mental-health-treatment-delivery-server may send information relating to the response (e.g., stress level, time of day, location, module presented, etc.). In some cases, the mental-health-treatment-delivery-server may provide multiple types of information to electronic health record server 106.

In an additional example, the mental-health-treatment-delivery-server may also include a machine learning component that analyzes the interactions of a user with the client device and the VR medical therapy environment to determine times to recommend that a user interact with the mental-health-treatment-delivery-server or that a specific module might fit the predicted user's needs. In some cases, the mental-health-treatment-delivery-server may predict, using the machine learning, the next stage (higher or lower) of stress for a particular patient. The mental-health-treatment-delivery-server may record each prediction and the truth results for comparison and additional learning purposes.

FIGS. 4-8 depict various aspects of the mental-health-treatment-delivery-server that may be presented on a client device as described with regards to FIGS. 1-3.

Figure 4:
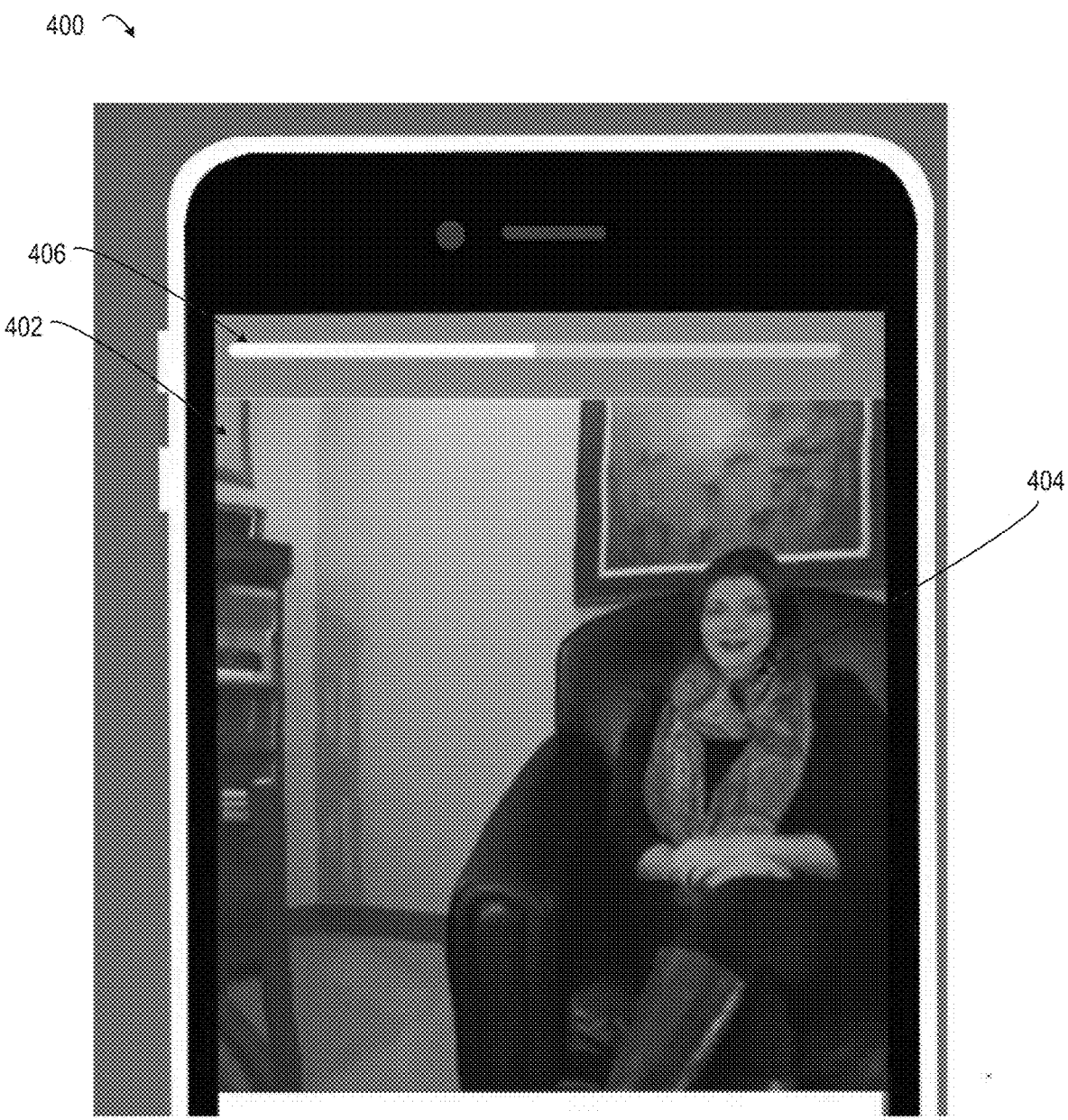
FIG. 4 depicts an example of a segment of video content as described with regards to FIGS. 1-3, according to some aspects of the disclosure.

FIG. 4 depicts an example of a segment of video content presented on a user device 400 as described with regards to FIGS. 1-3. The particular example of FIG. 4 illustrates a segment of VR video content 402 including a therapist 404 providing a mental health treatment.

The mental-health-treatment-delivery-server may present segments of video content, audio content, or VR content based on the performance of the user. For example, mental-health-treatment-delivery-server may provide a treatment module including the segment of VR video content 402 to the user device for presentation to the user. The mental-health-treatment-delivery-server can determine, based on the user's historical performance or responses to questions or stimuli, that a particular treatment module including the segment of VR video content 402 matches the condition of the user. The mental-health-treatment-delivery-server may present a treatment module that includes including the segment of VR video content 402 with a therapist 404 that provides a first type of mental health treatment.

In other examples, the mental-health-treatment-delivery-server may determine that the condition of a user matches a live segment of VR video content 402 with the therapist 404. The live segment of VR video content 402 may include an interactive mode that allows the therapist 404 to provide a second type of mental health treatment. The therapist 404 may request responses from the user during presentation of the treatment module. The mental-health-treatment-delivery-server can transmit the responses from the user as described with regard to FIGS. 1-3. The segment of VR video content 402 may include a progress bar 406 that indicates to the user a duration of the treatment module.

Figure 5:
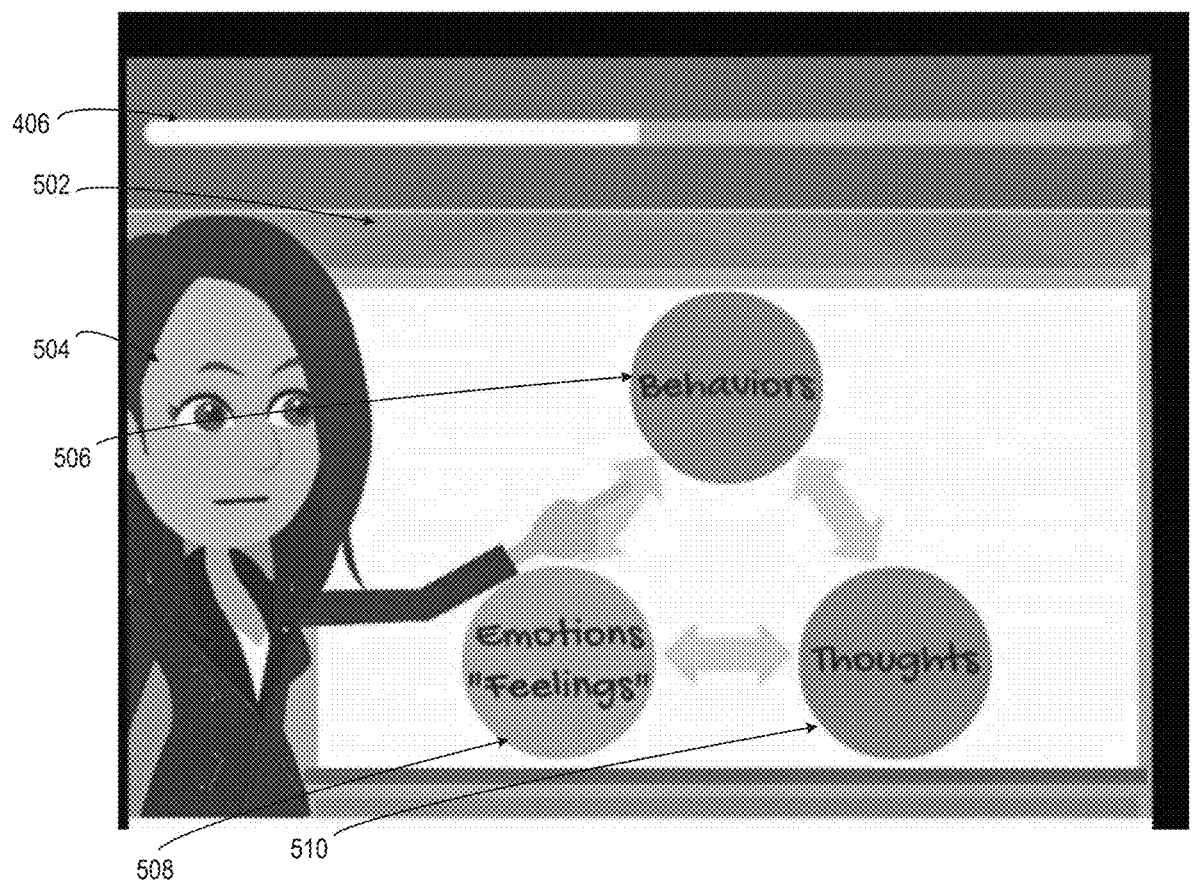
FIG. 5 illustrates an example of a module presented by a user device, according to some aspects of the disclosure.

FIG. 5 illustrates an example of a module 500 presented by a user device, according to some aspects of the disclosure. The particular example of FIG. 5 illustrates a combination of visual text content and a virtual therapist.

The mental-health-treatment-delivery-server may present segments of video or audio content that are accompanied by an interactive treatment environment. For example, mental-health-treatment-delivery-server may provide an interactive treatment environment 502 including a segment of VR video content that includes a virtual therapist 504 to the user device for presentation to the user. The mental-health-treatment-delivery-server can determine, based on the user's historical performance or responses to questions or stimuli, that a particular treatment module can be presented using the interactive treatment environment 502 and the virtual therapist 504. The mental-health-treatment-delivery-server may present, in the interactive treatment environment 502, a treatment module that includes multiple segments of VR video content. The interactive treatment environment 502 may receive inputs from the user, such as selection of a portion of the screen by a gesture, which selects a sub-module of the treatment module. For instance, the interactive treatment environment 502 may include selectable options for behaviors sub-module 506, emotions "feelings" sub-module 508, thoughts sub-module 510. The interactive treatment environment 502 may present each sub-module in a predetermined sequence, or alternatively, based on the user selected sub-module.

In other examples, the interactive treatment environment 502 can present a subset of the sub-modules, such as one or more of sub-module 506, emotions "feelings" sub-module 508, thoughts sub-module 510 based on performance of the user during one or more of the sub-modules. The mental-health-treatment-delivery server may adjust a sequence of sub-modules, omit a sub-module, or replay a sub-module according to the user's performance. The interactive treatment environment 502 may include a progress bar 406 that indicates to the user a total duration of all sub-modules, or a segment duration for a current sub-module being presented.

Figure 6:
FIG. 6 illustrates another example of a module presented by a user device, according to some aspects of the disclosure.

FIG. 6 illustrates another example of a module 600 presented by a user device, according to some aspects of the disclosure. The particular example of FIG. 6 illustrates a contextual situation designed to elicit an emotional or mental reaction from the user. The mental-health-delivery server may provide feedback to the user, similar to as described with regard to FIGS. 1-5 relating to a user's response to the contextual situation. In some instances, the user may provide a response to the contextual situation via an answer to a question, a rating of stress level, an emotional description, or the like. In other instances, the mental health treatment application can detect, using sensors of the user device, features that indicate the response of the user. Examples include audio or vibration sensors that can detect verbal sounds of the user or hand tremor/shaking, respectively.

Figure 7:
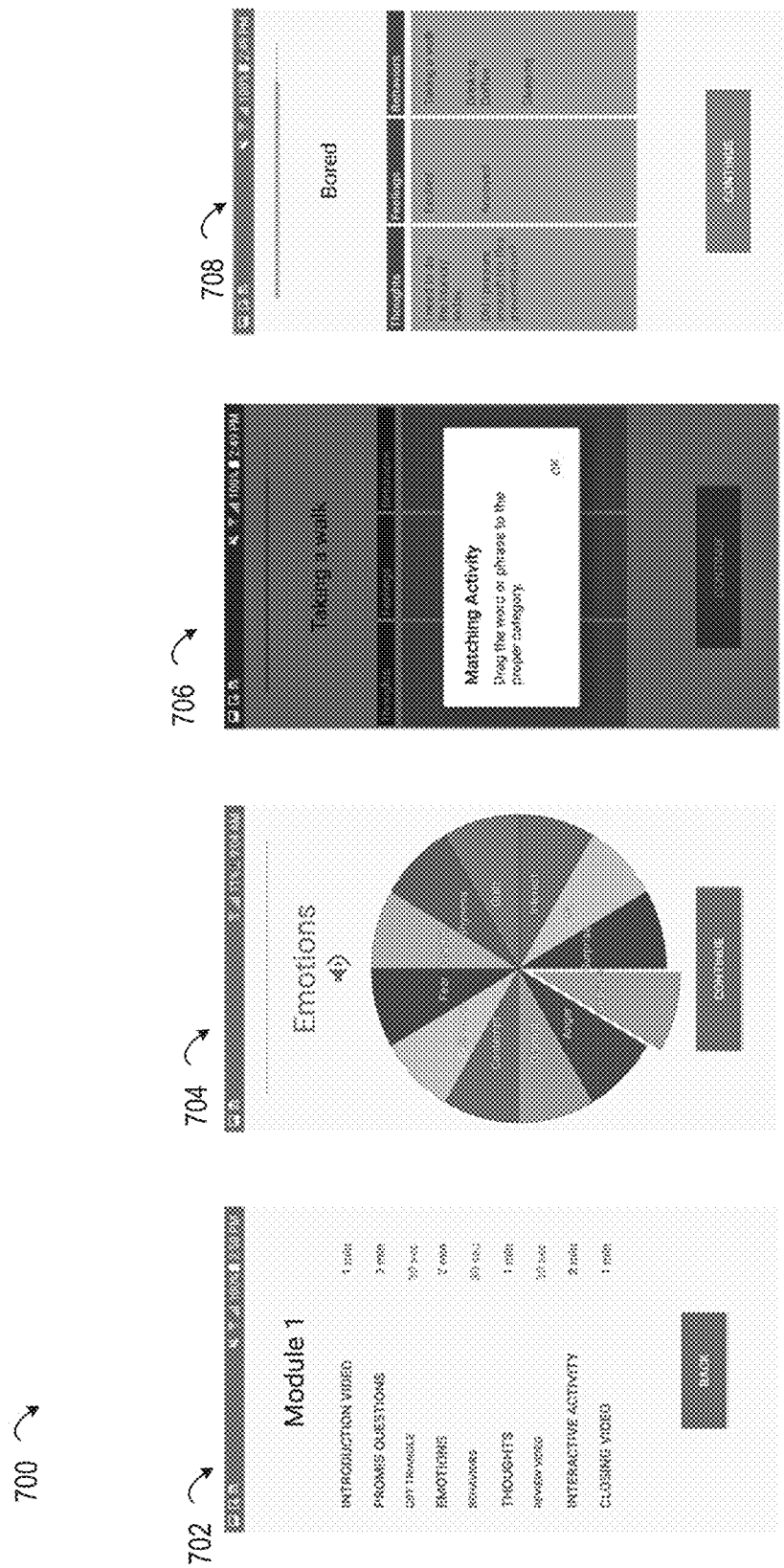
FIG. 7 depicts various user interface elements provided by the user device, according to some aspects of the disclosure.

FIG. 7 depicts various user interface elements provided by the user device. The examples illustrated by FIG. 7 depict examples of content of a module 700, including a module overview page 702, various emotional responses 704, a matching activity instruction 706, and mental therapy explanatory content 708. The module 700 and the user interface elements may be provided from mental-health-treatment-delivery server to the user device.

Figure 8:
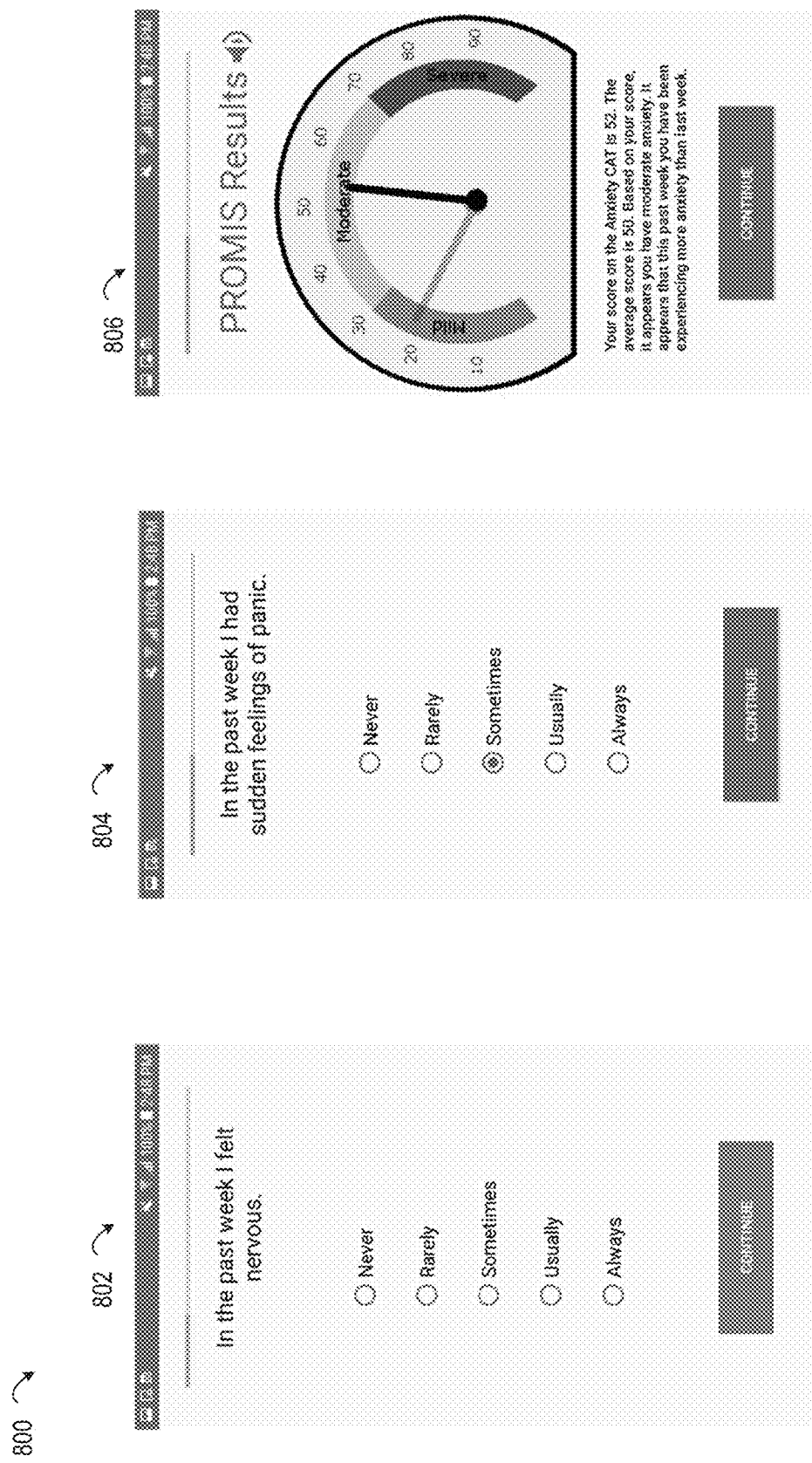
FIG. 8 depicts examples of questions to a user and feedback information presented to the user, according to some aspects of the disclosure.

FIG. 8 depicts examples 800 of questions to a user and feedback information presented to the user. The particular examples 800 of FIG. 8 illustrate a question 802 to which a response from the user 804 is received, and a user feedback score 806 is determined by the mental-health-treatment-delivery-server. The mental-health-treatment-delivery server may provide the question 802, receive the response from user input to the user device, and provide the user feedback score 806 to the user device.

While the present subject matter has been described in detail with respect to specific aspects thereof, it will be appreciated that those skilled in the art, upon attaining an understanding of the foregoing, may readily produce alterations to, variations of, and equivalents to, such aspects. Any aspects or examples may be combined with any other aspects or examples. Accordingly, it should be understood that the present disclosure has been presented for purposes of example rather than limitation, and does not preclude inclusion of such modifications, variations, or additions to the present subject matter as would be readily apparent to one of ordinary skill in the art.

What is claimed is:

1. A method comprising:

receiving, at a server device, at least one response to a question or stimuli presented to a user in connection with a mental health treatment application executing on a user device;

comparing the at least one response to stored user data to determine information to be presented to the user;

outputting an instruction for causing the mental health treatment application to output the information to the user, wherein outputting the instruction causes the user device to adjust visual lighting intensities to simulate conducting medical therapy sessions at a selected time of day, a particular weather condition, or a selected office environment lighting condition; and transmitting data about use of the mental health treatment application by the user to an electronic health record system.

2. The method of claim 1, wherein outputting the instruction comprises:

determining that the at least one response indicate that the user is moving toward an elevated stress level; and providing a calming module of content for presentation to the user.

3. The method of claim 1, wherein outputting the instruction comprises:

determining that the at least one response indicate a significant degradation in performance or increase in stress; and providing an emergency notification indicating that the user requires emergency treatment.

4. The method of claim 1, wherein outputting the instruction comprises:

determining that the at least one response indicates a change in performance of the user;

presenting, responsive to the change representing an improvement, an encouragement content item to reinforce the change in performance of the user; and presenting, responsive to the change representing a degradation, an admonishment content item to reduce the change in performance of the user.

5. The method of claim 1, wherein the information to be presented to the user comprises a therapy module that includes a parameters of a virtual therapist office, wherein the parameters include audio, video, or location cue.

6. The method of claim 1, further comprising:

determining a data structure of the electronic health record system;

extracting a set of features from the data about use of the mental health treatment application;

matching one or more features of the set of features with an element of the data structure; and storing, in the electronic health record system, the one or more features that correspond to the element of the data structure.

7. A system comprising:

a processor; and a non-transitory memory device communicatively coupled to the processor comprising instructions that are executable by the processor to cause the processor to perform operations comprising:

outputting, by a user device, a module with video content in connection with a mental health treatment protocol for a user;

outputting a request for the user to respond to a question or to stimuli;

receiving a response from the user to the question or the stimuli;

transmitting the response to a server device for comparing the response to stored data to determine information to present to the user;

receiving a command from the server device to present the information to the user; and outputting the information to an interface of the user device, wherein outputting the information includes causing the user device to adjust visual lighting intensities to simulate conducting medical therapy sessions at various times of day, various weather conditions, or various office environment lighting conditions.

8. The system of claim 7, wherein the operation of outputting the information comprises:

determining that the response from the user indicates that the user is moving toward an elevated stress level; and providing the information including a calming module of content for presentation to the user.

9. The system of claim 7, wherein the operation of outputting the information comprises:

determining that the response from the user indicates a significant degradation in performance or increase in stress; and providing an emergency notification indicating that the user requires emergency treatment.

10. The system of claim 7, wherein the operation of outputting the information comprises:

determining that the response from the user indicates a change in performance of the user;

presenting, responsive to the change representing an improvement, an encouragement content item to reinforce the change in performance of the user; and presenting, responsive to the change representing a degradation, an admonishment content item to reduce the change in performance of the user.

11. The system of claim 7, wherein the information comprises a therapy module that includes a parameters of a virtual therapist office, wherein the parameters include audio, video, or location cue.

12. The system of claim 7, wherein the operations further comprise:

determining a data structure of an electronic health record system;

extracting a set of features from the data about use of the mental health treatment protocol;

matching one or more features of the set of features with an element of the data structure; and storing, in the electronic health record system, the one or more features that correspond to the element of the data structure.

13. A non-transitory computer-readable medium comprising instructions that are executable by a processing device to perform operations comprising:

outputting, by a user device, a module with video content in connection with a mental health treatment protocol for a user;

outputting a request for the user to respond to a question or to stimuli;

receiving a response from the user to the question or the stimuli;

transmitting the response to a server device for comparing the response to stored data to determine information to present to the user;

receiving a command from the server device to present the information to the user; and outputting the information to an interface of the user device, wherein outputting the information includes causing the user device to adjust visual lighting intensities to simulate conducting medical therapy sessions at various times of day, various weather conditions, or various office environment lighting conditions.

14. The non-transitory computer-readable medium of claim 13, wherein the operation of outputting the information comprises:

determining that the response from the user indicates that the user is moving toward an elevated stress level; and providing a calming module of content for presentation to the user.

15. The non-transitory computer-readable medium of claim 13, wherein the operation of outputting the information comprises:

determining that the response from the user indicates a significant degradation in performance or increase in stress; and providing an emergency notification indicating that the user requires emergency treatment.

16. The non-transitory computer-readable medium of claim 13, wherein the operation of outputting the information comprises:

determining that the response from the user indicates a change in performance of the user;

presenting, responsive to the change representing an improvement, an encouragement content item to reinforce the change in performance of the user; and presenting, responsive to the change representing a degradation, an admonishment content item to reduce the change in performance of the user.

17. The non-transitory computer-readable medium of claim 13, wherein the information to be presented to the user comprises a therapy module that includes a parameters of a virtual therapist office, wherein the parameters include audio, video, or location cue.

18. The non-transitory computer-readable medium of claim 13, wherein the operations further comprise:
   determining a data structure of an electronic health record system;
   extracting a set of features from the data about use of the mental health treatment protocol;
   matching one or more features of the set of features with an element of the data structure; and
   storing, in the electronic health record system, the one or more features that correspond to the element of the data structure.

19. The non-transitory computer-readable medium of claim 13, wherein the module with video content comprises a plurality of video segments associated with a stress level of the user.

20. The non-transitory computer-readable medium of claim 19, wherein each video segment of the plurality of video segments includes an interactive treatment environment comprising a therapist, a customizable environment, an audio cue, and a video cue.

* * * * *